(12) United States Patent
Bansal

(10) Patent No.: US 8,802,063 B2
(45) Date of Patent: Aug. 12, 2014

(54) COSMETIC COMPOSITION

(75) Inventor: Amitabh Bansal, Hoboken, NJ (US)

(73) Assignee: Avon Products, Inc., New York, NY (US)

( * ) Notice: Subject to any disclaimer, the term of this patent is extended or adjusted under 35 U.S.C. 154(b) by 408 days.

(21) Appl. No.: 12/980,815

(22) Filed: Dec. 29, 2010

(65) Prior Publication Data

US 2012/0171131 A1 Jul. 5, 2012

(51) Int. Cl.
| | | |
|---|---|---|
| A61K 8/81 | (2006.01) | |
| A61Q 1/04 | (2006.01) | |
| A61Q 17/04 | (2006.01) | |
| A61Q 5/00 | (2006.01) | |
| A61Q 3/02 | (2006.01) | |

(52) U.S. Cl.
CPC ............... *A61K 8/8105* (2013.01); *A61Q 5/00* (2013.01); *A61Q 3/02* (2013.01); *A61Q 1/04* (2013.01)
USPC .................... 424/59; 424/61; 424/63; 424/64

(58) Field of Classification Search
None
See application file for complete search history.

(56) References Cited

U.S. PATENT DOCUMENTS

| | | | |
|---|---|---|---|
| 5,218,049 A | 6/1993 | Yamamoto et al. | |
| 5,853,642 A | 12/1998 | Siedle et al. | |
| 6,180,123 B1 | 1/2001 | Mondet | |
| 2005/0171310 A1 | 8/2005 | Oshima et al. | |
| 2006/0013791 A1 * | 1/2006 | Shimizu et al. | 424/70.12 |
| 2006/0067960 A1 * | 3/2006 | Russ et al. | 424/401 |
| 2007/0104667 A1 * | 5/2007 | Mondet et al. | 424/70.7 |
| 2007/0190011 A1 * | 8/2007 | Jacques et al. | 424/70.7 |

FOREIGN PATENT DOCUMENTS

EP 0726291 A1 * 8/1996

* cited by examiner

*Primary Examiner* — Hasan Ahmed
*Assistant Examiner* — Randeep Singh
(74) *Attorney, Agent, or Firm* — David M. Joyal; Joan M. McGillycuddy

(57) ABSTRACT

Provided are cosmetic and personal care compositions having film-formers that are copolymers of olefins and cycloolefins, such as ethylene/propylene/ethylidenenorbornene terpolymers. The compositions may provide long wearing, transfer resistant and/or highly comfortable films on the lips, skin, hair and nails.

38 Claims, No Drawings

COSMETIC COMPOSITION

FIELD OF INVENTION

The present invention relates generally to cosmetic compositions having long-wearing attributes. More specifically, the invention relates to cosmetic compositions that have polymeric film formers comprising copolymers of olefins and cycloolefins, such as ethylene/propylene/ethyl idenenorbornene terpolymers.

BACKGROUND OF THE INVENTION

Lip products, such as lipsticks and lip glosses, are used to impart color and shine to the lips. Most of these conventional lip products are mixtures of waxes, oils, and colorants. A notable drawback to these products is the tendency of the color to transfer from the lips onto a substrate that comes into contact with the lips, including napkins, fingers, clothes, drinking glasses, and the like. As a consequence, the desired effect is lost after a short amount of time and the product must be re-applied several times throughout the day.

Some success in imparting longer-wear and transfer resistance to lip products has been achieved through the use of film forming polymers which act to fix the colorants at the site of application and reduce transfer of the product from the lips. For example, L'Oreal's U.S. Pat. No. 6,180,123 to Mondet discloses the use of crystalline olefin copolymers in cosmetics which are said to impart supple, flexible and non-sticky films which are resistant to water. The crystalline olefin copolymers can be, for example, a copolymer of an alpha-olefin and of a cycloolefin, such as an ethylene/norbornene copolymer.

There is a continuing need in the art for cosmetic film formers that impart desired attributes such as long-wear, transfer resistance, and comfort to the integuments to which the cosmetic is applied.

It is therefore an object of the invention to provide improved cosmetic and personal care products having film formers which, when applied to the surface of an integument, product films that are long-wearing yet comfortable and which, when used in a pigmented or colored composition, reduces the tendency of the color to migrate from the surface.

SUMMARY OF THE INVENTION

In accordance with the foregoing objectives and others, the present invention provides compositions and methods for imparting films on human integuments, including hair, lashes, nails, lips, and skin.

In one aspect of the invention, a composition for application to a human integument is provided comprising an effective amount of a film-forming copolymer of one or more olefins and one or more cycloolefins. The film-forming copolymer is preferably substantially non-crystalline, preferably free of crystallinity, and/or is liquid at room temperature. The one or more olefins will typically comprise ethylene and/or propylene, and the one or more cycloolefins will typically comprise a norbornene monomer, such as norbornene or ethylidenenorbornene.

In one implementation, film-forming copolymer comprises ethylene, propylene and ethylidenenorbornene where the mole ratio of ethylene to propylene is between about 1:99 to about 99:1, more typically between about 40:60 to about 80:20, and the ethylidenenorbornene comprises from about 0.1 to about 20% by weight of the copolymer, more typically from about 7.5 to about 12.5% by weight of the copolymer.

The polymer may be, for example, the terpolymer ethylene/propylene/ethyl idenenorbornene.

In a related aspect, a cosmetic composition for application to a human integument is provided comprising an effective amount of a film-forming terpolymer having the structure of Formula (III):

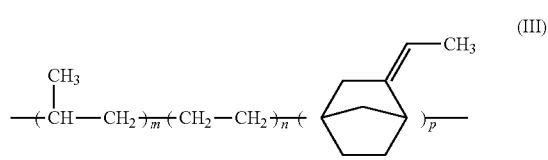

where m, n, and p are integers selected to provide a copolymer having an ethylidenenorbornene content from about 0.1% to about 20% by weight of the copolymer, a mole ratio of ethylene to propylene between about 1:99 to about 99:1, the terpolymer being substantially non-crystalline and/or having a molecular weight sufficiently low render the copolymer liquid at room temperature.

In another aspect, the compositions may further comprise a colorant (e.g., a pigment, pearlescent, lake, or dye) in combination with an effective amount of a film-forming copolymer of one or more olefins and one or more cycloolefins, wherein said film-forming copolymer is substantially non-crystalline and/or is liquid at room temperature, including without limitation the film-forming terpolymer of Formula (III). These compositions exhibit superior resistance to transfer or migration of the colorant from a human integument, including the lips, as compared to an otherwise identical composition wherein the film-forming polymer is copolymer of only the olefins but not the cylcoolefins, which is to say that, in the case of an ethylene/propylene/ethylidenenorbornene terpolymer, that the inventive composition exhibits improved resistance to transfer as compared to an otherwise identical composition where the film former is a biopolymer of ethylene and propylene having the identical mole ratio of ethylene:propylene as in the inventive film-former. A method is also provided for imparting a transfer-resistant color cosmetic film on a human integument, such as the lips, comprising applying such a composition to the integument.

Also provided is a method for imparting a glossy film on the lips or nails comprising applying to said lips or nails a composition comprising a film-forming copolymer of one or more olefins and one or more cycloolefins, wherein said film-forming copolymer is substantially non-crystalline and/or liquid at room temperature, including without limitation the film-forming terpolymer of Formula (III). Where the compositions are formulation as a nail polish, the film forming polymers may be dissolved or dispersed in isododecane (IDD) as a vehicle, which enables the formulation of acetate-free and nitro-cellulose-free nail polishes.

In yet another aspect of the invention, a method for imparting a cross-linked film on a human integument is provided. In this method, a composition is applied to the integument comprising (a) a film-forming copolymer of one or more olefins and one or more cycloolefins, wherein said film-forming copolymer is substantially non-crystalline and/or liquid at room temperature and includes a two or more reactive functional groups, (b) a cross-linking agent having at least two functional groups reactive with said reactive functional groups of the film-forming copolymer; and (c) optionally, one or more reagents selected from the groups consisting of polymerization catalysts, polymerization initiators, and polymerization inhibitors, effective to modulate the onset or rate of cross-linking; and optionally, applying heat or light to the composition on the integument, to thereby cross-link said copolymer with said cross-linking agent in situ on the surface of said integument.

In one embodiment, the film forming polymer is an ethylene/propylene/ethylidenenorbornene terpolymer and the cross-linking agent will comprises, by way of illustration, either a hydrocarbon polymer having at least two terminal olefinic groups reactive with the ethylidenenorbornene or a silicone polymer having silane groups reactive with the ethylidenenorbornene.

In one implementation of this method for in situ cross-linking, the film-forming copolymer is the terpolymer of Formula (III), and the cross-linking agent is a polyfunctional monomer or polymer reactive with the ethylidene groups of said terpolymer. This method is particularly suitable for application to hair of the head, where cross-linking may be affected by, for example, applying heat with a blow-dryer. The method may be used to increased curl retention in the hair.

These and other aspects of the present invention will become apparent to those skilled in the art according to the present description, including the claims.

DETAILED DESCRIPTION

The present invention provides compositions and methods for forming films on human integuments, including the hair of the scalp, eyelashes, skin, and nails.

The compositions comprise an effective amount of a film-forming copolymer of one or more olefins and one or more cycloolefins. By "effective amount" is meant an amount sufficient to measurably increase the substantivity of the cosmetic on the surface of the integument, and will typically be from about 0.01% to about 80% by weight of the cosmetic composition, more typically from about 0.1% to about 50% by weight, preferably from about 1% to about 30% by weight, and more preferred still, from about 5% to about 20% by weight. The term "copolymer" is intended to include bipolymers, terpolymers, quaterpolymers, or the like. The copolymers of the invention may be, without limitation, random, alternating, or block copolymers.

In one embodiment, the film-forming copolymer is substantially non-crystalline at room temperature, by which is meant the degree of crystallinity, if any, is less than 2%, but typically will be less than 1%, preferably less than 0.5%, and more preferred still, less than 0.1% by weight of the copolymer. The crystallinity can be modulated by controlling the relative aboundance or atacticm, isotactic and syndiotactic units or blocks in the copolymers. Atactic region will tend to prevent crystallinity due to their amorphous nature, whereas isotactic and syndiotactic regions will confer crystallinity and should be kept relatively low or absent, as will be evident to one skilled in the art.

In some embodiments, the film-forming copolymers are copolymers olefins and cycloolefins, wherein the olefins and/or cycloolefins consist essentially of specific monomers. In this context, the term "consist essentially of" is intended to exclude any additional monomers, the presence or amounts of which would measurably increase the crystallinity, render the polymers solid or semi-solid at room temperature, and/or otherwise diminish the long-wear, transfer-resistance, or comfort of the resulting film.

The copolymers are also preferably liquid at room temperature. As used herein, room temperature is 25° C. It is within the skill in the art to determine the appropriate molecular weight range required to provide a liquid polymer, however, the range will typically vary from about 100 Daltons (Da) to about 1,000,000 Da, but will more typically be from about 1,000 Da to about 100,000 Da. The film-forming copolymers are also preferably soluble in isododecane (IDD) and/or other aliphatic hydrocarbon solvents, preferably soluble at room temperature.

As used herein, the term "long-wear" means that the composition retains a freshly applied appearance for an extended period of time, for example, at least one hour, at least two hours, at least six hours, at least eight hours, or even twelve hours or more, under conditions of normal use. A film is transfer-resistant if it displays a decreased propensity to transfer colorant to a substrate on contact therewith as compared to an otherwise identical composition in the absence of the film-former. Preferably, the films of the invention are also comfortable, which means that they are elastic and do not pull tightly on the skin or lips. The comfort may be measured on the basis of consumer or expert panel testing as is well known in the cosmetics field.

The copolymers are the reaction products of (i) one or more olefins and (ii) one or more cycloolefins. Without wishing to be bound by any particular theory, it is believed that the cycloolefin content decreases the oil solubility of the polymer and also provides hard segments which have greater substantivity with the surface of the integument. The preferred copolymers according to the invention will provide greater transfer resistance, longer wear, and/or improved comfort as compared to otherwise identical copolymers that lack the cyloolefin content. It is also believed that the copolymers of the invention will provide greater transfer resistance, longer wear, and/or improved comfort as compared to more highly insoluble and/or crystalline copolymers of olefins and cycloolefins, such as those described in U.S. Pat. No. 6,180,123, the disclosure of which is hereby incorporated by reference for all purposes. In some embodiments, the compositions of the invention will be free of any of the insoluble and/or crystalline polymers of U.S. Pat. No. 6,180,123.

The cycloolefins may be any cyclic hydrocarbon having at least one double bond between adjacent carbon atoms within a ring. Typically, these will be $C_4$-$C_{20}$ hydrocarbons, more typically, $C_5$-$C_{14}$ hydrocarbons, and may comprise more than one fused ring system, optionally comprising from 1 to 6 heteroatoms, such as oxygen, sulfur, or nitrogen in the ring system. By way of illustration, the cycloolefins may be selected from the group consisting of cyclobutene, cyclohexene, cycolpentadiene, dicylcopentadiene, cyclooctadiene, dicyclopentadiene, norbornene, norbornadiene, 5-norbornene-2,3-dicarboxylic anhydride, norbornene diene, norbornene styrene, norbornene maleic anhydride, norbornene silane, norbornene siloxane, dimethanooctahydronaphthalene, ethylidenenorbornene, tetracyclododecene, vinylbenzocyclobutane, 4-vinylcyclohexene, vinylnorbornene, and combinations thereof.

Other suitable cycloolefins include, without limitation, the products of the Diels Alder reaction between an optionally substituted cyclopentadiene or furan and a linear or cyclic olefin. In a preferred embodiment the cycloolefin is a norbornene compound, by which is meant that the compound includes in its structure the norbornene ring system. In one embodiment, the cycloolefin comprises or consists essentially of norbornene.

In a preferred embodiment, the cycloolefin monomer will have the structure of formula (I):

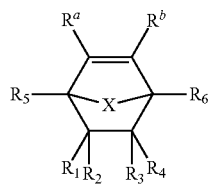

(I)

wherein, X is selected from —O—, —S—, —N($R^N$)$_2$—, —C(O)—, —C(R*)$_2$—, —C(R*)$_2$C(R*)$_2$—, —C(R*)$_2$—O—, —C(R*)$_2$—N($R^N$)$_2$—, —C(O)C(R*)$_2$—, —C(O)—O—, —C(O)—N($R^N$)$_2$—, but will preferably be —CH$_2$—;

$R^a$ and $R^b$ are each independently selected from the group consisting of hydrogen, halogen, $C_1$-$C_6$ alkyl, $C_1$-$C_6$ alkenyl, $C_1$-$C_6$ alkynyl, aryl, cyano, and —C(O)OR*, but are preferably each hydrogen;

$R_1$, $R_2$, $R_3$, and $R_4$ are each independently selected from the group consisting of hydrogen, halogen, hydroxyl, cyano, vinyl, —N($R^N$)$_2$, —C(O)OR*, —C(O)N($R^N$)$_2$, —S(O)$_2$R*, or a $C_1$-$C_{16}$ hydrocarbon selected from alkyl, haloalkyl, hydroxyalkyl, alkenyl, alkynyl, allyl, aryl, aryl-alkyl, and alkyl-aryl; wherein any one of $R_1$ or $R_2$ or any one of any one of $R_3$ or $R_4$ may be absent in which case the remaining substituent of $R_1$ and $R_2$ or of $R_3$ and $R_4$ forms a double bond with the ring carbon atom to which it is attached to form an alkylidene substituent; and wherein any of $R_1$, $R_2$, $R_3$, and $R_4$ may together form additional ring systems having from three to eight atoms in the ring;

$R_5$ and $R_6$ are each independently selected from the group consisting of hydrogen, halogen, methyl, ethyl, propyl, butyl; vinyl, allyl, and butenyl, but are typically each hydrogen; and $R^N$ and R* are, independently at each occurrence, selected from hydrogen or a $C_1$-$C_{16}$ alkyl, alkenyl, alkynyl, aryl, aryl-alkyl, or alkyl-aryl group; and wherein any one or more of $R^N$ and R* may, together with another of $R^N$ or R*, form additional ring systems having from three to six ring atoms.

In one embodiment of the compounds of Formula (I), X is —C(R*)$_2$—, where R* is preferably hydrogen at both occurrences, and $R^a$, $R^b$, $R_5$, and/or $R_6$, are hydrogen. In another embodiment, X is —CH$_2$—, and $R^a$, $R^b$, $R_5$, and $R_6$, are hydrogen. In another embodiment, X is —CH$_2$—, and $R^a$, $R^b$, $R_5$, and $R_6$, are hydrogen, and $R_2$ is absent, such that $R_1$ together with the ring carbon to which it is attached forms a $C_1$-$C_{12}$ alkylidene group of the form of Formula (II):

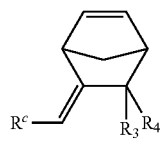

(II)

where $R^c$ a $C_1$-$C_{10}$ hydrocarbon group, typically an aliphatic hydrocarbon group, preferably an alkyl group, and more preferably a $C_1$-$C_4$ alkyl group.

In various embodiments according to Formula (II), $R^c$ is methyl, ethyl, propyl, or butyl, and $R_3$ and $R_4$ are each hydrogen. In a preferred embodiment, $R^c$ is methyl and the monomer is ethylidenenorbornene. In one embodiment, the cycloolefin will comprise or consist essentially of ethylidenenorbornene.

The cycloolefins will comprise from 0.001% to about 99% by weight of the copolymers, typically from about 0.01% to about 75% by weight, more typically from about 0.1% to about 20% by weight, and preferably, from 5% to about 15%, and more preferably from about 7.5% to about 12.5% by weight. In one embodiment, norbornene and/or ethylidenenorbornene will comprise from about 0.1% to about 20% by weight, more typically from 5% to about 15% by weight, and preferably from about 7.5% to about 12.5% by weight of the copolymer.

The copolymers are also derived from olefins, and will typically consist predominantly of ethylene and/or propylene. The ethylene and/or propylene will typically comprise from about 50% to about 99.9% by weight of the copolymer, more typically from about 70% to about 98%, and more typical still, from about 85% to about 95% by weight of the copolymer. In one embodiment, the mole ratio of ethylene to propylene is between about 1:99 to about 99:1, but is more typically between about 20:80 to about 90:10, and preferably between about 40:60 to about 80:20.

The film-formers may also be formed from additional monomers, including without limitation, $C_4$-$C_{10}$ alpha-olefins. Non-limiting examples of $C_4$-$C_{10}$ alpha-olefins include 1-butene, 1-pentene, 1-hexene, 1-octene, 1-nonene, 1-decene, 1-undecene, 1-dodecene, 3,5,5-trimethyl-1-hexene, 3-methyl-1-pentene, and 4-methyl-1-pentene, to name a few.

Other monomers polymerizable with the cycloolefin and/or olefins may also be included. Mention may be made of isobutylene, isoprene, styrene, alkylstyrene, (meth)acrylic acid, and (meth)acryltates. Moreover, suitably functionalized polymers may be reacted with the oefinic polymers to impart desired functionality. These include, without limitation, siloxanes (e.g., dimethylsiloxane), polyurethanes, polyesters, polyamides, polyethers, and the like, which have been suitably functionalized to react with the olefin and/or cycloolefins. For example, the forgoing polymers may be functionalized with terminal alkenes and may be reacted with the olefin and/or cycloolefins using standard Ziegler-Natta catalysts.

In a preferred embodiment, the film-forming copolymer has the structure of Formula (III):

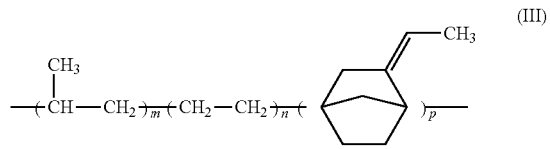

(III)

where m, n, and p are integers selected to provide a copolymer having an ethylidenenorbornene content from about 0.1% to about 20% by weight of said copolymer, typically between about 5% and about 15%, and more typically between about 7.5% and about 12.5%, a mole ratio of ethylene to propylene between about 1:99 to about 99:1, more typically between about 20:80 to about 90:10, and preferably between about 40:60 to about 80:20, such that the copolymer is substantially non-crystalline and/or has a molecular weight sufficiently low render the copolymer liquid at room temperature.

The molecular weight of the copolymer will typically be in the range of 100 to 1,000,000 Daltons, but should ideally be such that the polymer is liquid at room temperature, rather than semi-solid or solid. In one embodiment, the molecular weight of the copolymer will be between 2,500 and 150,000 Daltons, or between about 5,000 and about 75,000 Daltons, or between about 7,500 and about 50,000. Terpolymers of ethylene/propylene/ethylidenenorbornene are available under the Trilene™ line from Lion Copolymer. Trilene™ 67 is said to have an ethylene/propylene ratio of 45/55, an ethylidenenorbornene content of 9.5%, and a molecular weight of about 7,700 Da. Trilene™ 77 is said to have an ethylene/propylene ratio of 75/25, an ethylidenenorbornene content of 10.5%, a molecular weight of about 7,500 Da, and a melting transition by DSC between 50-60° C.

In some, but not all, embodiments, the compositions may include additional film-forming polymers other than copolymers of olefins and cycloolefins. Particular mention may be made of polymers that provide good transfer-resistance, including silicone acrylate copolymers, such as those having the INCI names Butyl Acrylate/Hydroxypropyl Dimethicone Acrylate Copolymer (CTFA Monograph ID 12998), Acrylates/Dimethicone Copolymer (CTFA Monograph ID 10082), and Acrylates/Ethylhexyl Acrylate/Dimethicone Methacrylate Copolymer (CTFA Monograph ID 16592). Other suitable film formers include, without limitation, polyolefins, polyamides, polyesters, polyimides, polyurethanes, acrylates, and the like.

In some embodiments, the compositions may include from about 0.1% to about 50%, typically from about 1% to about 20%, by weight of a wax component. The waxes may be low melt waxes such as higher chain alkanes, including for example, n-octadecane (MP~28-30° C.), n-nonadecane (MP~32° C.), and n-eicosane (MP~37° C.), or high melt waxes including, without limitation, many traditional waxes that are derived, for example, from animals, insects, vegetables, minerals, or petroleum, as well as synthetic waxes, Fisher Tropsch waxes, and mixtures of any of the foregoing waxes. Specific mention is made of carnauba, paraffin wax, candelilla, castor, beeswax, microcrystalline wax, ceresin, ozokerite, polyethylene wax, low MW polyalkyacrylate, and silicone waxes, such as alkyl silicones, or any combinations thereof.

The cosmetic and personal care compositions according to the invention will typically comprise the film-forming copolymer dissolved or dispersed in a vehicle suitable for topical use, either cosmetically, pharmaceutically, and/or dermatologically. The vehicle may be aqueous or anhydrous. It may be in the form of an emulsion, including a water-in-oil, oil-in-water, silicone-in-water, water-in-silicone emulsion, triple-emulsions or the like. When the compositions are formulated as an emulsion, they will typically comprise from about 0.1% to about 10% by weight of a suitable emulsifier.

The vehicle may be aqueous or anhydrous. By "anhydrous" is meant that no water is intentionally added to the formulation but does not exclude minor amounts of water associated with the other components as impurities, but in any event means less than 2.5% by weight water, typically less than 1% by weight water, and more typically, less than 0.5% by weight water, based on the entire weight of the composition.

The vehicle may comprise an oil, including for example, a hydrocarbon oil, ester oil, and/or silicone oil. In one embodiment, the vehicle comprises isododecane (IDD), in either an anhydrous or emulsified state. The oil phase of the emulsion may include, for example, vegetable oils; esters such as octyl palmitate, isopropyl myristate and isopropyl palmitate; ethers such as dicapryl ether; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; additional natural or synthetic waxes; and the like. Suitable hydrophobic hydrocarbon oils may be saturated or unsaturated, have an aliphatic character and be straight or branched chained or contain alicyclic or aromatic rings. The oil-containing phase may be composed of a singular oil or mixtures of different oils.

The cosmetic compositions of the invention may optionally include one or more agents that provide or enhance shine. Shine enhancing agents will typically have a refractive index greater than about 1.4, preferably greater than about 1.5 when measured as a film at 25° C. Suitable shine enhancing agents include without limitation, polyols (e.g., glycerin), fatty esters, silicone oils, phenylpropyldimethylsiloxysilicate, polybutene, polyisobutene, hydrogenated polyisobutene, hydrogenated polycyclopentadiene, propyl phenyl silsesquioxane resins; lauryl methicone copolyol, perfluorononyl dimethicone, dimethicone/trisiloxane, methyl trimethicone, and combinations thereof. In one embodiment, the composition will comprise a shine-enhancing agent in an amount from about 0.1% to about 10% by weight, more preferably from about 1% to about 5% by weight, based on the total weight of the composition.

In some embodiments, the compositions further comprise a colorant. As used herein, the term "colorant" includes any material added to impart a hue or optical effect to the composition, and includes without limitation pigments, pearls, lakes, and dyes. The composition may comprise colorants in an amount from about 0.1% to about 90% based on the entire weight of the composition, but typically will comprise from about 0.5% to about 20% by weight, and more typically from about 1% to about 10% by weight colorants.

Suitable colorants are well known in the art and are disclosed in the C.T.F.A. Cosmetic Ingredient Handbook, First Edition, 1988, the contents or which are hereby incorporated by reference. Organic dyes include, for example, FD&C dyes and D&C dyes. Lakes include those based on barium, strontium, calcium or aluminum. Exemplary inorganic pigments include, but are not limited to, metal oxides and metal hydroxides such as iron oxides, iron hydroxides, titanium dioxide, zirconium oxides, cerium oxides, chromium oxides, chromium hydroxides, manganese oxides, and zinc oxides. Other suitable colorants include carbon black, ultramarine blue, ferric blue, Prussian blue, manganese violet, talc, mica, sericite, calcium carbonate, fumed silica, and the like. Suitable pearling pigments include, without limitation, bismuth oxychloride, guanine, and titanated mica. The colorants may be surface modified, for example with Triethoxy Caprylylsilane, to adjust one or more characteristics of the colorant, such as dispersibility in the vehicle.

In some embodiments, the color cosmetics will comprise and alkyl silane surface-treated colorant comprising an alumina substrate (e.g., platelet shaped) and a pigment, dye, or lake bonded to the alumina substrate by an alkyl silane surface treatment. Typically, the alkyl silane will be octylsilane and may be formed by treatment with Triethoxy Caprylylsilane. Non-limiting examples of such colorants include, but are not limited to, the COVALUMINE™ line by SENSIENT™ Cosmetic Techologies LCW.

In addition to color cosmetics, the films may be incorporated into any product where it is desirable to hold a functional agent in contact with a biological surface or integument. In addition to pigments, lakes, dyes, opacifiers, and pearling agents, the functional agent may be, for example, insect repellants, sunscreens, UV absorbers, UV blockers, antiperspirants, conditioners, tooth whiteners, and the like. The film-forming copolymers may be useful in a variety of cosmetic and personal care products, including without limitation, lipsticks, lip glosses, and lip colors, water-proof mascaras, transfer-resistant foundations, nitro-cellulose-free and acetate-free nail enamels, water-proof sunscreens and insect repellents, skin care products, hair care products (including shampoos, conditioners, styling gels, creams and mousses), tooth-whitening products, antiperspirants and deodorants, to name a few.

The compositions of the invention may optionally comprise other functional agents that are active and inactive ingredients typically associated with any of the foregoing cosmetic and personal care products, including, but not limited to, excipients, fillers, emulsifying agents, antioxidants, surfactants, film formers, chelating agents, gelling agents, waxes, thickeners, emollients, humectants, moisturizers, vitamins, minerals, viscosity and/or rheology modifiers, sunscreens, keratolytics, depigmenting agents, retinoids, alpha-hydroxy acids, antibacterial agents, antifungal agents, antimicrobials, antivirals, anti-acne agents, skin cooling compounds, skin protectants, skin penetration enhancers, exfollients, fragrances, depigmenting agents, self-tanning agents, preservatives, stabilizers, pharmaceutical agents, and mixtures thereof. In addition to the foregoing, the cosmetic and personal care products of the invention may contain any other compound for the treatment of skin disorders.

In some embodiments, the compositions exhibits superior resistance to transfer of colorants from a human integument, such as the lips, as compared to an otherwise identical composition wherein said film-forming copolymer does not comprise a content of cycloolefin, such as ethylidenenorbornene. Accordingly, one embodiment of the invention is a method for imparting a transfer-resistant color cosmetic film on a human integument (skin, lips, nails, hair, lashes, etc.) comprising applying to the surface of the integument a coating of a composition comprising a colorant and an effective amount of a film-forming copolymer having the structure of Formula (III) to reduce migration of the colorant from the surface.

It has also been observed that the film-forming copolymers of the invention are capable of imparting a shiny film on a human integument (skin, lips, nails, hair, lashes, etc.), which makes them ideal for lip products, such as lip sticks and lip glosses, as well as nail polishes.

In some embodiments, the film-forming copolymers of the invention will comprise a plurality of reactive functional groups that permit the copolymer to be cross-linked, optionally by an appropriate cross-linking agent, such as a monomer or polymer having two or more groups that are reactive with the functional groups of the copolymer. In one embodiment, the copolymer will possess two or more, preferably a plurality, and more preferably between about one and about 25 mol percent, typically between about 5 and about 15 mol percent, of a reactive olefin. The copolymer can be cross-linked through the reactive olefins by treatment with heat, light, evaporation of a volatile inhibitor, or with an appropriate initiator or catalyst. In some embodiments, the cross-linking reaction occurs in situ on the surface of the integument.

In one embodiment in situ cross-linking of the copolymer on the surface a human integument is accomplished by contacting the surface with copolymer having the structure of Formula (III), optionally with a cross-linking agent having at least two functional groups reactive with the ethylidene group; and effecting the reaction through the application of heat, light, or UV, or contacting the copolymer with a polymerization catalyst. Alternatively, the composition may be formulated with a volatile agent which inhibits the cross-linking reaction but which evaporates after application to the integument to thereby allow the polymerization to proceed.

If a cross-linking agent is employed, it will be a species having two or more reactive functional groups capable of forming a covalent bond to the copolymer, for example by reacting with the ethylidene group in the terpolymer of Formula (III). The cross-linking agent could, for example, comprise a silicone polymer having at least two silane groups reactive with ethylidenenorbornene through a hydrosilylation reaction, or may be a polyolefin, polyether, polyester, polyurethane, polysiloxane, polyamide, or the like, having at least two terminal olefinic groups reactive with said ethylidenenorbornene through standard Ziegler Natta chemistry.

In one embodiment, the compositions are applied to human hair to form a film over the surface of the hair. The copolymers can optionally be cross-linking by, for example, heating the hair with a blow-dryer or the like. In one embodiment, hair that has been treated with the film-forming copolymers of the invention maintains curl for longer as compared to the case where an otherwise identical composition is applied to the hair which employs a like film-former without a cycloolefin content, for example, an ethylene/propylene biopolymer having an identical ratio of ethylene:propylene as the ethylene/propylene/ethylidenenorbornene terpolymers of Formula (III).

EXAMPLE 1

The ability of two ethylene/propylene/ethylidenenorbornene terpolymers (Trilene™ 67 and Trilene™ 77) to inhibit migration of colorants from a surface was investigates in comparison to that of two ethylene/propylene bipolymers (Trilene™ CP1100 and Trilene™ CP80). The mole ratio of ethylene to propylene and the cycloolefin content of the copolymers tested is provided in table I.

TABLE I

| Copolymer | Ethylene:Propylene | Cycloolefin (%) |
|---|---|---|
| Trilene ™ 67 | 44:55 | 9.5 |
| Trilene ™ 77 | 75:25 | 10.5 |
| Trilene ™ CP1100 | 40:60 | — |
| Trilene ™ CP80 | 43:57 | — |

The polymers were each formulated into cosmetic compositions consisting of isododecane vehicle and red iron oxide pigment, as shown below in Table II.

TABLE II

| Ingredient | A | B | C | D |
|---|---|---|---|---|
| Trilene ™ 67 | 45% | — | — | — |
| Trilene ™ 77 | — | 45% | — | — |
| Trilene ™ CP1100 | — | — | 45% | — |
| Trilene ™ CP80 | — | — | — | 45% |
| red iron oxide | 10% | 10% | 10% | 10% |
| IDD | 45% | 45% | 45% | 45% |

The ability of each of Samples A-D to prevent pigment transfer was determined using the transfer resistance test protocol described in U.S. Pat. No. 6,071,503, the disclosure of which is hereby incorporated by reference. Briefly, a film of each cosmetic is applied to a collagen sheet and a portion of the film is contacted with water and another portion is contacted with oil. Styrofoam discs is then applied with pressure on top of the regions of the film that were challenged with water and oil, respectively, an turned in place 360°. The amount of colorant transferred to the Styrofoam disc is then evaluated on a scale of 1 to 5 where: 5=no transfer, 4=less than half of the Styrofoam disc is colored, 3=about half of the Styrofoam disc is covered, 2=more than half is covered, and 1=all of the Styrofoam disc is covered. The results are shown below in Table III.

TABLE III

| Sample | Water | Oil |
|--------|-------|-----|
| A | 4 | 5 |
| B | 5 | 5 |
| C | 1 | 3 |
| D | 3 | 4 |

As shown, the film forming copolymers having a content of cycloolefin exhibit unexpectedly superior transfer-resistance as compared to like copolymers which do not include cycloolefins.

Samples A and B were also evaluated for comfort using a model based on the weight loss of a film when stretched on a rubber substrate. The model was validated as follows. Several commercially available lip products were cast on a rubber substrates in a 1×1 square inch area, such that 20 mg of solids remain behind after drying. The rubber substrates was pulled to three times their length and dusted using a nail polish brush. The sample was then re-weighed and the weight loss was plotted against the subjectively reported comfort. This model has been validated with a variety of film formers and demonstrates that films that exhibit a larger loss of weight on stretching are generally less comfortable, whereas those that show little weight loss are generally more comfortable. Samples A and B gave no observable weight loss, indicated that they are expected to provide maximum comfort. In contrast, similar formulations comprising either an MQ resin, styrene/polyisobutylstyrene (SIBS), polyamide, or polyacrylate film formers each showed weight losses ranging from 7% for the MQ resin to 19% for the SIBS polymer, indicating that the comfort was low to medium. It was unexpected that a copolymer of olefins and cycloolefins with provide high transfer resistance and high comfort.

The compositions will find use in a variety of cosmetic an personal care compositions, particularly those in which long wear is desirable. Representative examples include, without limitation, nail polishes, color cosmetics, cosmetics for the face, such as liquid or powder foundations, cosmetics for the eyes, such as mascara and eye shadow, and skin care products, such as lotions, creams, SPF products, etc., with and without actives for imparting a therapeutic benefit to an integument such as the skin.

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described therein will become apparent to those skilled in the art from the foregoing description. Such modifications are also intended to fall within the scope of the appended claims. All publications cited herein are incorporated by reference in their entirety.

The invention claimed is:

1. A topical composition for application to a human integument comprising an effective amount of a film-forming copolymer of one or more olefins and one or more cycloolefins, and a vehicle suitable for topical use, wherein said film-forming copolymer has less than 1% crystallinity by weight and is liquid at room temperature, and wherein said one or more cycloolefins consist essentially of a cycloolefin-of formula (I):

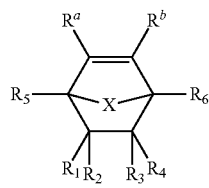

(I)

wherein,
X is selected from —O—, —S—, —N($R^N$)$_2$—, —C(O)—, —C(R*)$_2$—, —C(R*)$_2$C(R*)$_2$—, —C(R*)$_2$—O—, —C(R*)$_2$—N($R^N$)$_2$—, —C(O)C(R*)$_2$—, —C(O)—O—, —C(O)—N($R^N$)$_2$—;

$R^a$ and $R^b$ are each independently selected from the group consisting of hydrogen, halogen, $C_1$-$C_6$ alkyl, $C_1$-$C_6$ alkenyl, $C_1$-$C_6$ alkynyl, aryl, cyano, and —C(O)OR*;

$R_1$, $R_2$, $R_3$, and $R_4$ are each independently selected from the group consisting of hydrogen, halogen, hydroxyl, cyano, vinyl, —N($R^N$)$_2$, —C(O)OR*, —C(O)N($R^N$)$_2$, —S(O)$_2$R*, or a $C_1$-$C_{16}$ hydrocarbon selected from alkyl, haloalkyl, hydroxyalkyl, alkenyl, alkynyl, allyl, aryl, aryl-alkyl, and alkyl-aryl; wherein any one of $R_1$ or $R_2$ or any one of any one of $R_3$ or $R_4$ may be absent in which case the remaining substituent of $R_1$ and $R_2$ or of $R_3$ and $R_4$ forms a double bond with the ring carbon atom to which it is attached to form an alkylidene substituent; and wherein any of $R_1$, $R_2$, $R_3$, and $R_4$ may together form additional ring systems having from three to eight atoms in the ring;

$R_5$ and $R_6$ are each independently selected from the group consisting of hydrogen, halogen, methyl, ethyl, propyl, butyl; vinyl, allyl, and butenyl; and $R^N$ and R* are, independently at each occurrence, selected from hydrogen or a $C_1$-$C_{16}$ alkyl, alkenyl, alkynyl, aryl, aryl-alkyl, or alkyl-aryl group; and wherein any one or more of $R^N$ and R* may, together with another of $R^N$ or R*, form additional ring systems having from three to six ring atoms.

2. The composition according to claim 1, wherein the one or more olefins consist essentially of ethylene and/or a $C_3$-$C_{10}$ alpha-olefin.

3. The composition according to claim 1, wherein X is —C(R*)$_2$—, where R* is hydrogen at both occurrences, $R^a$, $R^b$, $R_5$, and $R_6$, are each hydrogen.

4. The composition according to claim 3, wherein $R_1$ and $R_2$ are each hydrogen, or $R_2$ is absent and $R_1$ together with the ring carbon to which it is attached forms a $C_1$-$C_{12}$ alkylidene group of the form of formula (II):

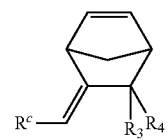

(II)

where $R^c$ is a $C_1$-$C_{10}$ alkyl group.

5. The composition according to claim 4, wherein $R_3$ and $R_4$ are each hydrogen, and $R^c$, if present, is methyl, ethyl, propyl, or butyl.

6. The composition according to claim 1, wherein said one or more olefins comprise ethylene, propylene, or both ethylene and propylene.

7. The composition according to claim 4, wherein said one or more olefins comprise ethylene, propylene, or both ethylene and propylene.

8. The composition according to claim 1, wherein said one or more olefins comprise a $C_3$-$C_{10}$ alpha-olefin.

9. The composition according to claim 8, wherein said $C_3$-$C_{10}$ alpha-olefin is selected from the group consisting of propylene, 1-butene, 1-pentene, 1-hexene, 1-octene, 1-nonene, 1-decene, 1-undecene, 1-dodecene, 3,5,5-trimethyl-1-hexene, 3-methyl-1-pentene, and 4-methyl-1-pentene.

10. The composition according to claim 7, wherein said one or more cycloolefins comprise norbornene and/or ethylidenenorbornene.

11. The composition according to claim 10, wherein the mole ratio of ethylene to propylene is between about 20:80 to about 90:10.

12. The composition according to claim 11, wherein the mole ratio of ethylene to propylene is between about 40:60 to about 80:20.

13. The composition according to claim 7, wherein said one or more cycloolefins comprises ethylidenenorbornene from about 0.1 to about 20% by weight of said copolymer.

14. The composition according to claim 13, wherein ethylidenenorbornene comprises from about 5 to about 15% by weight of said copolymer.

15. The composition of claim 1, further comprising a cross-linking agent having at least two functional groups reactive with said cycloolefin; and, optionally, one or more reagents selected from the groups consisting of polymerization catalysts, polymerization initiators, and polymerization inhibitors.

16. The composition of claim 4, further comprising a cross-linking agent having at least two functional groups reactive with said cycloolefin; and, optionally, one or more reagents selected from the groups consisting of polymerization catalysts, polymerization initiators, and polymerization inhibitors.

17. The composition according to claim 16, wherein said cross-linking agent comprises a silicone polymer having at least two silane groups reactive with said cycloolefin.

18. The composition according to claim 16, wherein said cross-linking agent comprises a hydrocarbon polymer having at least two terminal olefinic groups reactive with said cycloolefin.

19. The composition according to claim 4, further comprising one or more integument functional agents.

20. The composition according to claim 19, wherein the functional agent is selected from the group consisting of colorants, sunscreens, other film formers, biological active agents, waxes, shine enhancing agents, emollients, and compatible combinations thereof.

21. The composition according to claim 5, wherein the film-forming copolymer has the structure of formula (III):

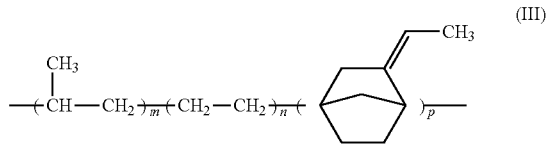

where m, n, and p are integers selected to provide a copolymer having an ethylidenenorbornene content from about 0.1% to about 20% by weight of said copolymer, a mole ratio of ethylene to propylene between about 1:100 to about 100:1.

22. The composition according to claim 21, wherein the ethylidenenorbornene content is from about 7.5 to about 12.5% by weight of said copolymer.

23. The composition according to claim 21, wherein the mole ratio of ethylene to propylene is between about 20:80 to about 90:10.

24. The composition of claim 21, further comprising a cross-linking agent having at least two functional groups reactive with said ethylidenenorbornene; and, optionally, one or more reagents selected from the groups consisting of polymerization catalysts, polymerization initiators, and polymerization inhibitors.

25. The composition according to claim 21, further comprising a functional agent selected from the group consisting of colorants, sunscreens, other film formers, biological active agents, waxes, shine enhancing agents, emollients, and compatible combinations thereof.

26. A topical composition for application to a human integument comprising an effective amount of a film-forming copolymer of one or more olefins and one or more cycloolefins, and a vehicle suitable for topical use, wherein said film-forming copolymer has less than 1% crystallinity by weight and is liquid at room temperature, and wherein the cycloolefin is a product of a Diels Alder reaction between an optionally substituted cyclopentadiene and a linear or cyclic olefin.

27. The composition according to claim 26, wherein the cycloolefin is selected from the group consisting of norbornene, norbornadiene, 5-norbornene-2,3-dicarboxylic anhydride, norbornene diene, norbornene styrene, norbornene maleic anhydride, norbornene silane, norbornene siloxane, ethylidenenorbornene, vinylnorbornene, and combinations thereof.

28. The composition according to claim 26, wherein the one or more olefins consist essentially of ethylene and/or a $C_3$-$C_{10}$ alpha-olefin.

29. A method for imparting a transfer-resistant color cosmetic film on a human integument comprising applying to said integument a composition comprising a colorant and an effective amount of a film-forming copolymer having the structure of Formula (III):

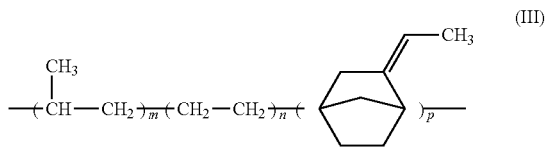

where m, n, and p are integers selected to provide a copolymer having an ethylidenenorbornene content from about 0.1% to about 20% by weight of said copolymer and a mole ratio of ethylene to propylene between about 1:100 to about 100:1, the copolymer having less than 1% crystallinity by weight and having a molecular weight sufficiently low render the copolymer liquid at room temperature;

wherein the composition exhibits superior resistance to transfer of said colorant from said integument as compared to an otherwise identical composition wherein said film-forming copolymer does not comprise ethylidenenorbornene.

30. The method according to claim 29, wherein the human integument is lips to which the applied composition imparts a glossy film.

31. The method according to claim 30, wherein the mole ratio of ethylene to propylene is between about 20:80 to about 90:10.

32. A method for imparting a cross-linked film on a human integument comprising:
(1) applying to said integument a composition comprising:
(a) a copolymer having the structure of Formula (III):

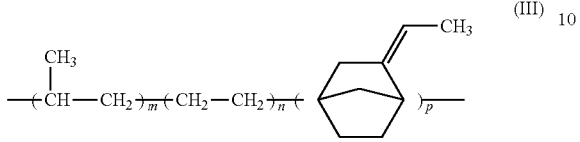

where m, n, and p are integers selected to provide a copolymer having an ethylidenenorbornene content from about 0.1% to about 20% by weight of said copolymer, a mole ratio of ethylene to propylene between about 1:99 to about 99:1, the copolymer having less than 1% crystallinity by weight and having a molecular weight sufficiently low render the copolymer liquid at room temperature;
(b) a cross-linking agent having at least two functional groups reactive with said ethylidenenorbornene; and
(c) optionally, one or more reagents selected from the groups consisting of polymerization catalysts, polymerization initiators, and polymerization inhibitors; and
(2) optionally, applying heat or light to said composition, to thereby cross-link said copolymer with said cross-linking agent.

33. The method according to claim 32, wherein said cross-linking agent comprises a silicone polymer having at least two silane groups reactive with said ethylidenenorbornene.

34. The method according to claim 32, wherein said cross-linking agent comprises a hydrocarbon polymer having at least two terminal olefinic groups reactive with said ethylidenenorbornene.

35. The method according to claim 32, wherein said integument is human hair.

36. The method according to claim 35, wherein step (2) comprises heating said hair with a blow-dryer.

37. The method according to claim 32, wherein the mole ratio of ethylene to propylene is between about 20:80 to about 90:10.

38. The method according to claim 32, wherein said human integument is nails.

* * * * *